United States Patent [19]
Dann et al.

[11] Patent Number: 5,755,236
[45] Date of Patent: May 26, 1998

[54] FEMALE INCONTINENCE DEVICE

[76] Inventors: Jeffrey A. Dann, 44 Terrace Dr., Worcester, Mass. 01609; David A. Gloth, 16 Harcourt St., Boston, Mass. 02116

[21] Appl. No.: 764,053
[22] Filed: Dec. 12, 1996
[51] Int. Cl.⁶ ............................................. A61F 5/48
[52] U.S. Cl. ................................. 128/885; 600/29
[58] Field of Search ...................... 128/885, DIG. 25, 128/830–841; 600/29–31

[56] References Cited

U.S. PATENT DOCUMENTS

| | | | |
|---|---|---|---|
| 1,982,001 | 11/1934 | Haas | 128/841 |
| 3,340,876 | 9/1967 | Hill | 128/295 |
| 3,349,768 | 10/1967 | Keane . | |
| 3,512,185 | 5/1970 | Ellis . | |
| 3,661,155 | 5/1972 | Lindan | 128/295 |
| 3,683,914 | 8/1972 | Crowley | 128/285 |
| 3,705,575 | 12/1972 | Edwards | 128/1 R |
| 3,776,235 | 12/1973 | Ratcliffe et al. | 128/283 |
| 3,958,564 | 5/1976 | Langguth | 128/2.06 E |
| 4,194,508 | 3/1980 | Anderson | 128/295 |
| 4,256,093 | 3/1981 | Helms et al. | 128/1 R |
| 4,421,511 | 12/1983 | Steer et al. | 604/329 |
| 4,484,917 | 11/1984 | Blackmon | 604/327 |
| 4,496,355 | 1/1985 | Hall et al. | 604/327 |
| 4,537,183 | 8/1985 | Fogarty | 128/DIG. 25 |
| 4,563,183 | 1/1986 | Barrodale et al. | 604/329 |
| 4,690,677 | 9/1987 | Erb | 604/329 |
| 4,795,449 | 1/1989 | Schneider et al. | 604/329 |
| 4,822,347 | 4/1989 | MacDougall | 604/329 |
| 4,846,819 | 7/1989 | Welch | 604/329 |
| 4,889,532 | 12/1989 | Metz et al. | 604/330 |
| 4,904,248 | 2/1990 | Vaillancourt | 604/329 |
| 5,074,855 | 12/1991 | Rosenbluth et al. | 604/385.1 |
| 5,090,424 | 2/1992 | Simon et al. | 128/885 |
| 5,131,906 | 7/1992 | Chen | 600/29 |
| 5,195,997 | 3/1993 | Carns | 604/347 |
| 5,234,409 | 8/1993 | Goldberg | 600/30 |
| 5,256,133 | 10/1993 | Spitz | 600/29 |
| 5,263,947 | 11/1993 | Kay | 604/331 |
| 5,336,208 | 8/1994 | Rosenbluth et al. | 604/329 |
| 5,509,427 | 4/1996 | Simon | 600/29 |

FOREIGN PATENT DOCUMENTS

| | | | |
|---|---|---|---|
| 947602 | 5/1974 | Canada | 128/110 |
| 0324557 | 7/1989 | European Pat. Off. | 128/918 |
| 1223353 | 6/1960 | France . | |
| 2542995 | 9/1984 | France | A61F 5/44 |
| 2817571 | 4/1978 | Germany | A61F 5/44 |
| 3633824 | 4/1988 | Germany | A61F 5/43 |
| 1467144 | 3/1977 | United Kingdom | A61F 5/44 |
| 2193438 | 10/1988 | United Kingdom | A61F 5/455 |
| WO9008561 | 9/1980 | WIPO | A61M 1/00 |
| WO9639989 | 12/1996 | WIPO . | |
| WO9639991 | 12/1996 | WIPO . | |

*Primary Examiner*—Michael A. Brown
*Attorney, Agent, or Firm*—Judith C. Crowley; Nutter, McClennen & Fish, LLP

[57] ABSTRACT

A device for alleviating female urinary incontinence comprising a resilient and at least partially deformable device body having a distal tip portion, a flange and an intermediate frustoconical portion extending outwardly from the tip portion to the flange. In use, upper wall portions of the intermediate frustoconical portion adjacent to the tip portion are moved toward abutting relation to form a first vacuum region within the tip portion and a second vacuum region within the frustoconical portion. The meatus of the user is disposed in the second vacuum region and is advantageously prevented from entering the first region by the upper wall portions of the intermediate frustoconical portion. With this arrangement, the meatus is disposed in a "tent" region (i.e., the second vacuum region) which has a broad base and an apex and is prevented from entering the first vacuum region which has a narrower entrance that could detrimentally entrap meatal tissue. The vacuum regions maintain the device in reliable sealed engagement with the meatal tissue.

13 Claims, 4 Drawing Sheets

3

FEMALE INCONTINENCE DEVICE

FIELD OF THE INVENTION

This invention relates generally to a device for alleviating female urinary incontinence and more specifically, to a device which maintains closure of the meatus urinarius to alleviate female urinary incontinence without causing discomfort or damage to the meatal tissue.

BACKGROUND OF THE INVENTION

Female urinary incontinence is a common problem throughout the world. Urinary incontinence can result from injuries sustained during childbirth, loss of urinary sphincter function, neurological disorders, trauma to the urethra and bladder neck and failed surgical repairs.

A variety of devices have been suggested to alleviate female urinary incontinence including catheters, urethral plugs, urethral collection devices, artificial intraurethral valves, vaginal pessaries and inflatable implantable prostheses. In general, these devices have been associated with problems of leakage, discomfort, inconvenience of use and urinary infection. Moreover, several of the devices are considered invasive and require surgical intervention for placement.

SUMMARY OF THE INVENTION

In accordance with the invention, a device for alleviating female urinary incontinence includes a device body having a distal tip portion, a flange and an intermediate frustoconical portion extending outwardly from the tip portion to the flange. The material of the device is resilient and at least partially deformable. In use, upper wall portions of the intermediate frustoconical portion adjacent to the tip portion are moved toward abutting relation to form a first vacuum region within the tip portion and a second vacuum region within the intermediate frustoconical portion. The meatus of the user is disposed in the second region and is prevented from entering the first region by the upper wall portions of the intermediate frustoconical portion.

Both the flange and the frustoconical portion have body contacting surfaces which, in use, contact meatal tissue. More particularly, at least a portion of the frustoconical side walls are disposed in contact with the meatus and serve to substantially close the meatus. The vacuum environment within the first and second regions maintains the device in reliable sealed engagement with the meatus.

The first and second vacuum regions may be separated by a closure formed by abutment of the upper frustoconical wall portions. Alternatively, a small gap may exist between the first and second vacuum regions. Advantageously however, any such gap is too small to permit meatal tissue to enter the first vacuum region, thereby preventing the tissue from being pinched or otherwise herniated at the junction between the regions. To this end, preferably, the side walls of the frustoconical portion have a length equal to or greater than one-half of the inner diameter of the flange.

With this arrangement, a "tenting" effect is created whereby the meatus is disposed in a tent region (i.e., the second vacuum region) which has a broad base, or entrance adjacent to the flange and an apex. Significantly, meatal tissue is prevented from entering the first vacuum region which has a narrower entrance by the apex of the tent region, thereby preventing meatal discomfort or damage by entrapment of tissue at the entrance to the first vacuum region.

Also described is a method for alleviating female urinary incontinence without causing meatal discomfort or damage.

The method includes the steps of deforming a device body having a distal tip portion, a flange and an intermediate frustoconical portion extending outwardly from the tip portion to the flange, by moving upper wall portions of the intermediate frustoconical portion adjacent to the tip portion toward abutting relation to form a first vacuum region within the tip portion and a second vacuum region within the intermediate frustoconical portion in which the meatus of the user is disposed. The upper frustoconical wall portions advantageously prevent meatal tissue from entering the first vacuum region. The method further includes the step of removing the device from the user's body to permit voiding.

BRIEF DESCRIPTION OF THE DRAWINGS

The foregoing features of this invention, as well as the invention itself, may be more fully understood from the following detailed description of the drawings in which.

DETAILED DESCRIPTION OF THE INVENTION

Figure 1:
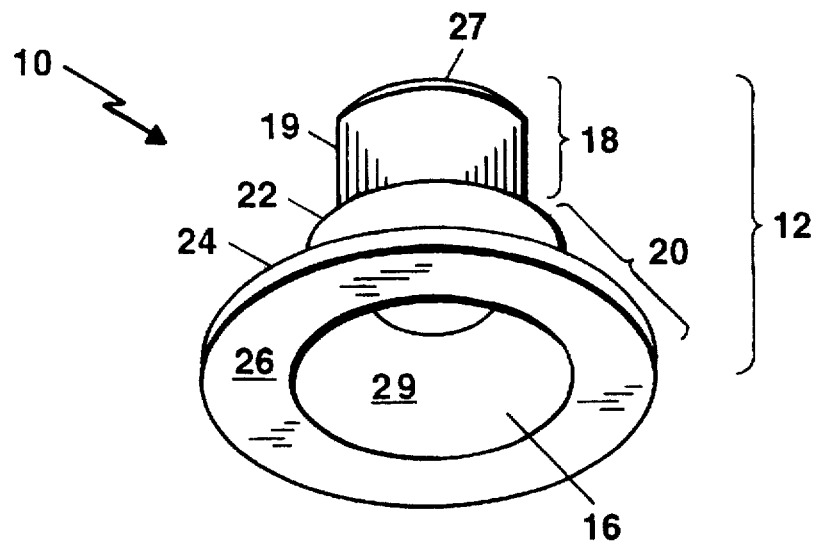
FIG. 1 is a perspective view of a female incontinence device in accordance with the invention.
Figure 2:
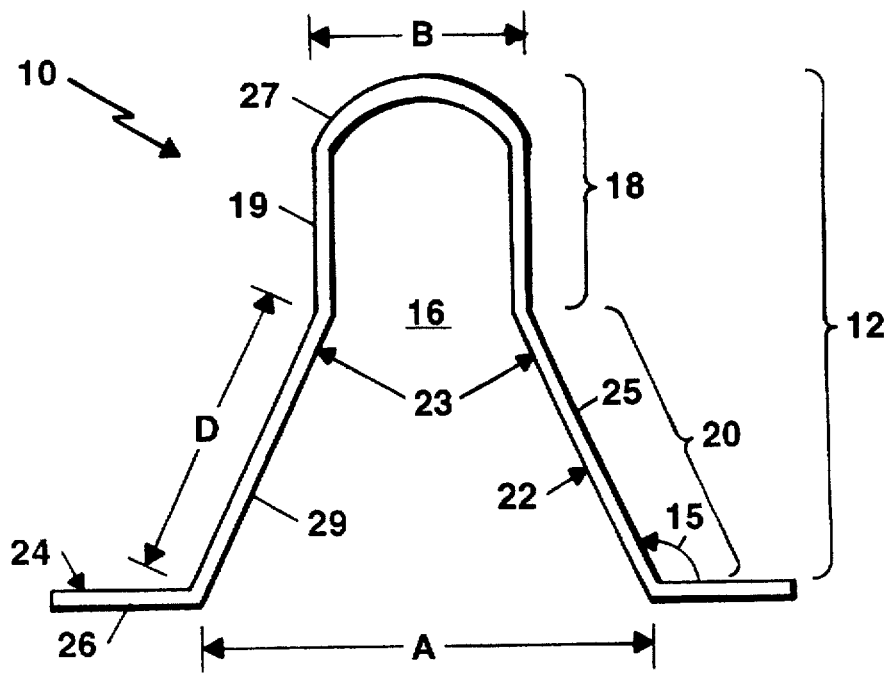
FIG. 2 is a cross-sectional side view of the device of FIG. 1.

Referring to FIGS. 1 and 2, a female urinary incontinence device 10 includes a device body 12 having a tip portion 18 distal from the user's body, a flange 24 and an intermediate frustoconical portion 22 extending outwardly from the tip portion to the flange. The device body 12 defines an interior chamber 16 extending from the curved outer end wall 27 of the tip portion 18 to the flange 24. A body contacting portion 20 of the device includes a body contacting surface 26 of the flange 24 and a body contacting surface 29 of the intermediate frustoconical portion 22.

In use, the body contacting surface 26 of the flange 24 contacts the tissue surrounding the meatus of the user's urethra and the body contacting surface 29 of the intermediate frustoconical portion 22 contacts and gently compresses the meatus. A vacuum environment formed within the chamber 16 during application of the device serves to maintain the device 10 in reliable sealed engagement with the user, as will be described. The tip portion 18 can collect a small amount of urine, although this does not generally occur. When voiding is necessary, the user readily removes the device 10.

The tip portion 18 has a substantially hemispherical shape with substantially vertical side walls 19 centered about a central longitudinal axis of the device and curved outer end wall 27 which serves as a gripping portion to facilitate application and removal of the device. In an alternate embodiment, the outer end wall 27 of the tip portion 18 is flat. The tip portion 18 must be at least partially deformable and, more particularly, compressible in order to produce at least a partial vacuum in the chamber 16 sufficient to seal the device 10 to the user's body by a differential in air pressure between the air within the chamber and the atmospheric air pressure. Specifically, an air and liquid seal is formed between the user's body and the device.

Figure 5:
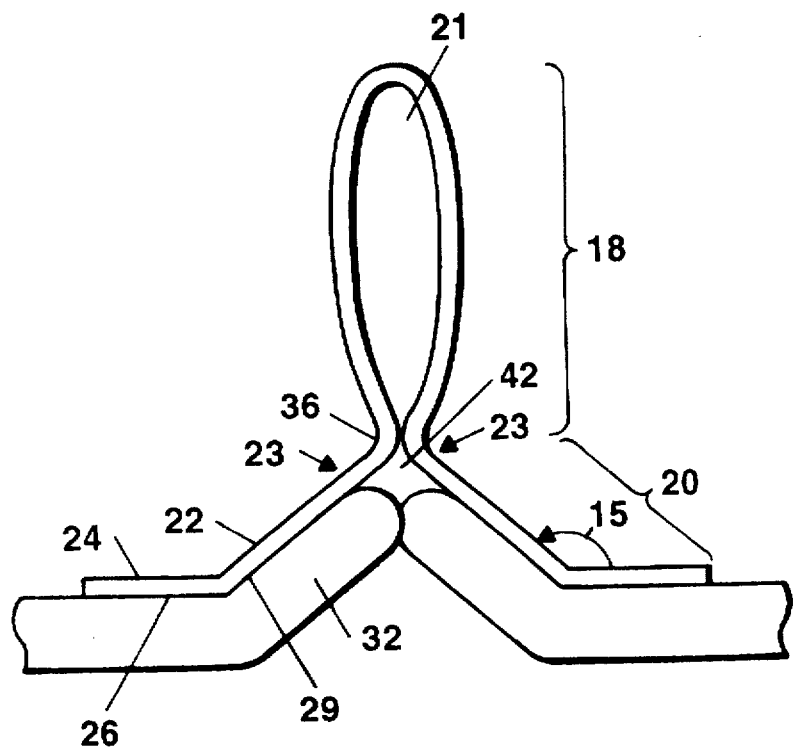
FIG. 5 is a cross-sectional side view of the device of FIG. 1 in use.
Figure 6:
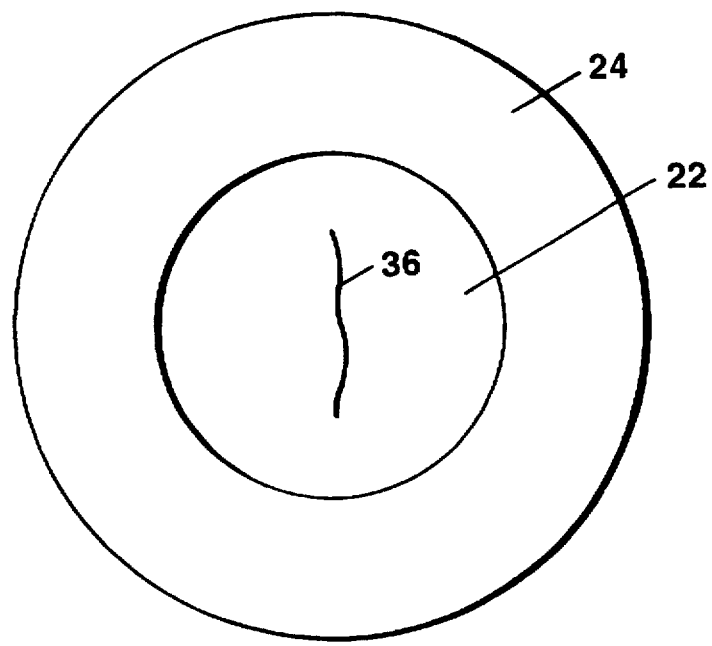
FIG. 6 is a bottom view of the device as shown in FIG. 5.

In use, at least a portion of the side walls 25 of the frustoconical portion 22 are disposed in contact with the meatal tissue 32 (FIG. 5). In this way, the frustoconical portion 22 provides closure to the user's meatus. Significantly, the frustoconical portion 22 is designed in such a way as to avoid causing discomfort or damage to the meatal tissue, as will become apparent.

The body contacting surface 26 of the flange 24 forms a continuous ring about the meatus and enhances the seal of the device to the user's body. More particularly, the flange 24 facilitates proper positioning of the device on the female user's body at the orifice of the urethra. If desired, the attachment of the device to the user's body may be enhanced with the use of an adhesive material disposed on the body contacting surface 26 of the flange 24 and the body contacting surface 29 of the frustoconical portion 22. Alternatively, a non-adhesive sealing material may be used to enhance the seal between the device and the user's body.

While the exact dimensions of the device 10 can vary without departing from the spirit of the invention, in general the device dimensions are dictated by the typical female anatomy. In particular, the inner diameter of the flange (labelled A) is generally between approximately 1.0–2.5 centimeters and, preferably, is approximately 2.0 centimeters. The inner diameter of the substantially hemispherical tip portion 18 (labelled B) can also vary, but in the preferred embodiment is on the order of 9.5 millimeters.

The length of the side walls 25 of the intermediate frustoconical portion 22 (labelled D) is preferably equal to or greater than one-half the inner diameter A of the flange 24. Thus, in the preferred embodiment in which the inner diameter A of the flange 24 is approximately 2.0 centimeters, the length D of the frustoconical side walls 25 is preferably at least 1.0 centimeter.

The angle 15 between the side walls 25 of the intermediate frustoconical portion 22 and the flange 24 is obtuse. Generally, the angle 15 is selected to allow the length D of the frustoconical side walls 25 to equal or exceed one-half the inner diameter A of the flange. In the above preferred embodiment, the angle 15 is between approximately 110 and 120 degrees.

Typically, the female urinary incontinence device 10 is of unitary construction. Alternatively however, the portions of the device 10 may be separately constructed and joined thereafter. The device 10 is comprised of any resilient and at least partially deformable material suitable for application to the human body in the manner described below. In the preferred embodiment, the device is comprised of FDA approved silicone or a thermoplastic elastomer, although urethane, latex or rubber material can be utilized.

Referring also to FIGS. 3–6, application of the device 10 to the user's body will be described. The user's meatus 32 is closed by gentle compression of the surrounding area. Closure of the meatus is maintained by two vacuum regions formed within the device body chamber 16 during application of the device, as will become apparent.

The device 10 is deformed by gently squeezing together the tip portion 18 and the upper wall portions 23 of the frustoconical side walls 25 (i.e., upper frustoconical side wall portions 23) adjacent to the tip portion 18. By squeezing portions 18 and 23, the upper frustoconical side wall portions 23 are moved, or gently urged inward toward abutting relation. This deformation of the device body 12 reduces the air volume in the chamber 16 and thereby creates at least a partial vacuum environment within the chamber. More particularly, as upper frustoconical side wall portions 23 are brought toward abutting relation, a first vacuum region 21 within the tip portion 18 and a second vacuum region 42 within the frustoconical portion 22 are formed, as shown in FIG. 5. The vacuum regions 21, 42 thus formed cause the device to be maintained in reliable sealed engagement with the user's body.

The meatal tissue 32 is disposed within the second vacuum region 42 defined by the frustoconical portion 22, with the body contacting surface 29 of the frustoconical portion 22 contacting meatal tissue. Significantly, the inwardly moved upper frustoconical side wall portions 23 prevent meatal tissue 32 from extending into the first vacuum region 21. In this way, meatal discomfort and/or damage otherwise caused by pinching of the tissue at the relatively narrow entrance to the first region is prevented.

The deformation of the device body 12 may form a closure between vacuum regions 21 and 42 as opposing upper frustoconical side wall portions 23 come into abutment at an apex 36, as shown in FIG. 5. Alternatively, a small gap between such opposing upper frustoconical side wall portions 23 may remain, albeit, such gap being too small to undesirably entrap meatal tissue. Note that even in instances when a small gap remains between opposing upper frustoconical side wall portions 23, two vacuum regions 21, 42 are still formed, with such regions being in communication through such gap.

The deformed device is placed over the meatus 32 and released, thereby permitting the device body 12 to expand to its original shape. This restorative deformation causes at least a partial vacuum to be provided in regions 21 and 42 by which the outside atmospheric pressure pushes the body contacting surface 26 of the flange 24 and the body contacting surface 29 of the frustoconical portion 22 against the meatal tissue 32.

When the deformed device is placed over the meatus 32, the intermediate frustoconical portion 22 is moved downward toward the meatus 32, thereby increasing the already obtuse angle 15 between the frustoconical side walls 25 and the flange 24. The length D of the frustoconical side walls 25 ensures that, as the device body 12 is deformed, the upper frustoconical side wall portions 23 come together in proximate abutting relation, thereby forming the first vacuum region 21 and the second vacuum region 42. Stated differently, the length D of the frustoconical side walls 25 is selected to prevent the walls 25 from becoming coplanar with respect to the flange (i.e., to prevent flattening of the frustoconical side walls 25) since such an arrangement could cause meatal tissue to become entrapped within the relatively narrow entrance, or base of the distal tip portion 18 and therefore cause pinching of the meatus. With the present device 10, a tenting effect is created, whereby the meatal tissue 32 is disposed in a "tent" region (i.e., the second vacuum region 42) which has a relatively broad base, or entrance and substantial height or distance from the meatus. Advantageously, meatal tissue 32 is prevented from entering the first vacuum region 21 which has a narrower base, or entrance, by an "apex" 36 of the tent at the upper frustoconical side wall portions 23. The entrance of the second vacuum region 42 has the same diameter as the inner flange diameter A which is broad relative to the diameter B of the tip portion 18. Furthermore, since meatal tissue 32 is not mobile or distensible, it is also prevented from entering the first vacuum region 21 because of the substantial height or distance of the tent apex 36 from the meatus created by the length of the frustoconical side walls 25.

Generally, the device 10 is brought into contact with the user's body already in its deformed state as shown in FIG.

Figure 3:
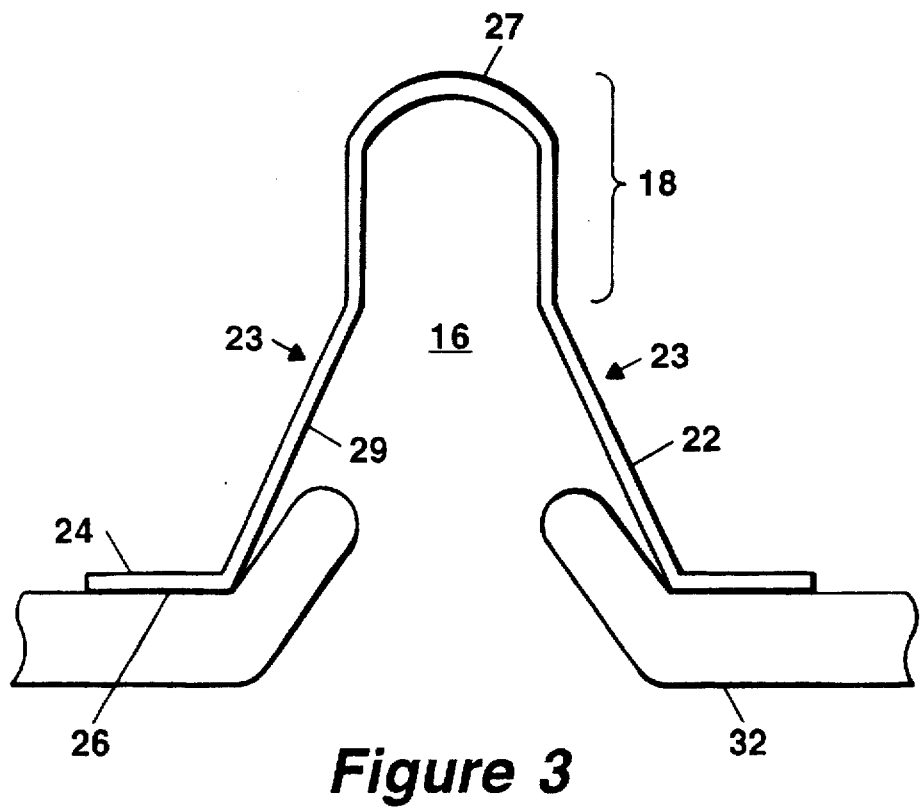
FIG. 3 is a cross-sectional side view of the device of FIG. 1 positioned over the meatus of a user, but not in use since no vacuum environment exists.
Figure 4:
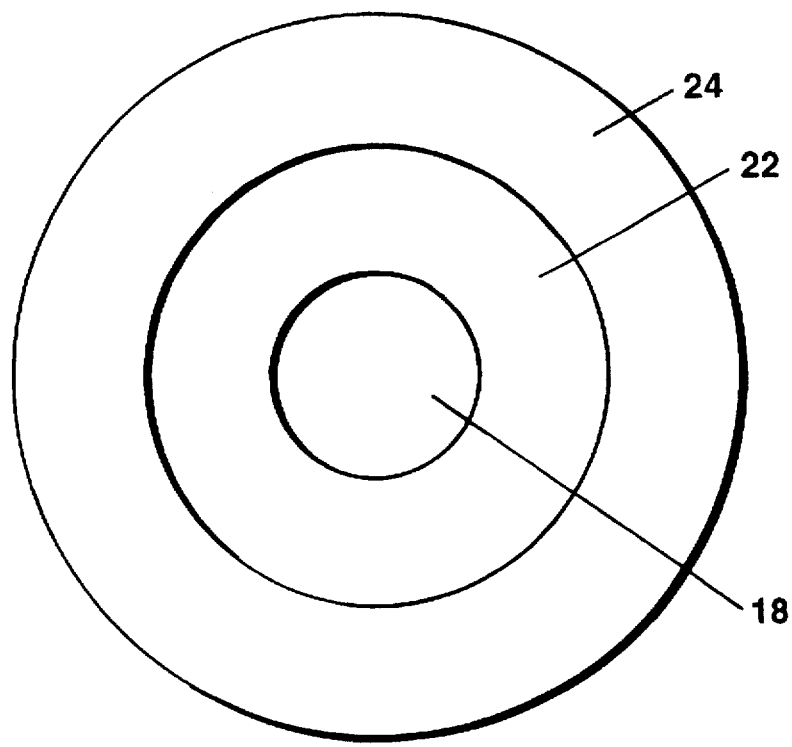
FIG. 4 is a bottom view of the device as shown in FIG. 3.

5. Alternatively however, the device may be brought into contact with the user's body prior to deformation (i.e., prior to formation of the vacuum regions 21 and 42), as shown in FIG. 3. In this case, once the device is placed over the meatus 32, the device body 12 is deformed in the above-described manner.

The device 10 is removed by the user to allow voiding when necessary. Specifically, the device can either be pulled off the skin directly or, preferably, the device body 12 is slightly depressed in order to reduce the pressure difference.

Figure 7:
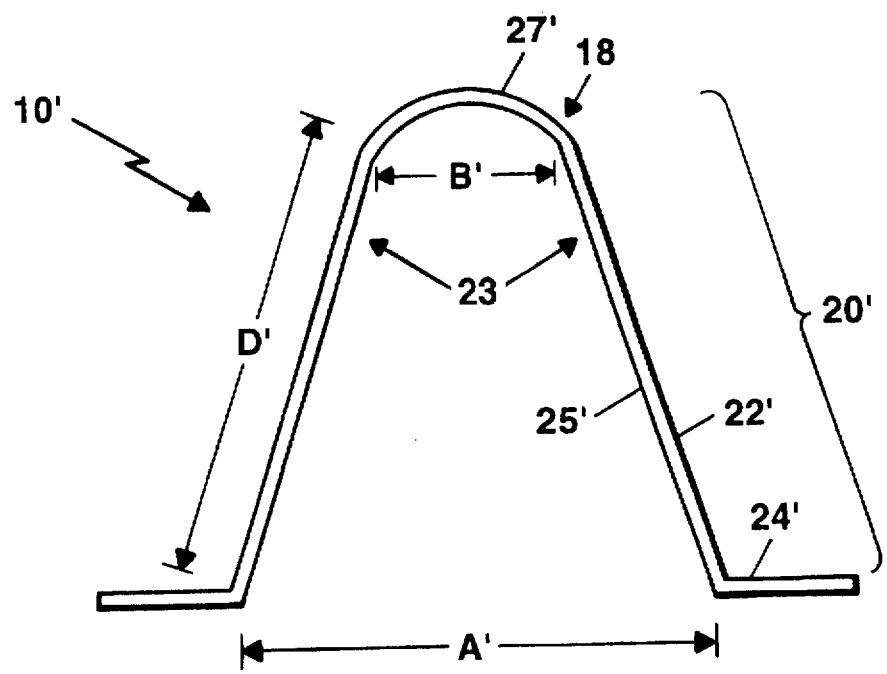
FIG. 7 is a cross-sectional side view of a female incontinence device in accordance with a further embodiment of the invention.
Figure 8:
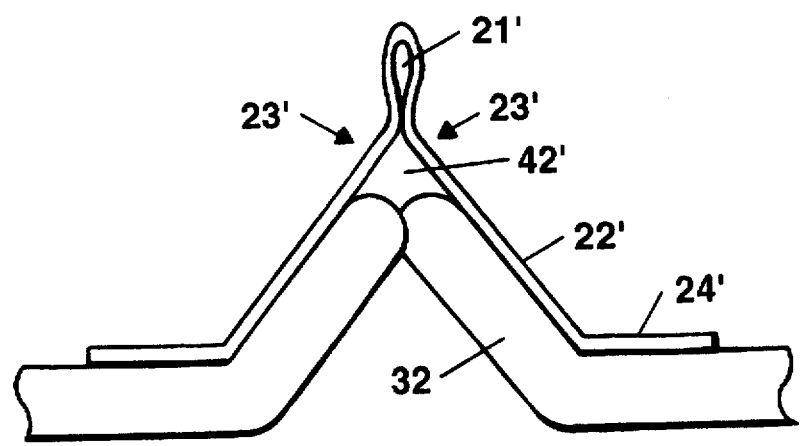
FIG. 8 is a cross-sectional side view of the device of FIG. 7 in use.

It will be appreciated that the shape of the various portions of the device, such as the flange 24 and tip portion 18, can be modified without departing from the spirit of the invention. As one example, an alternate embodiment 10' of the female incontinence device is shown in FIGS. 7 and 8. The device 10' differs from the device 10 of FIGS. 1–6 in that the intermediate frustoconical side walls 25' intersect the tip portion 18' at the start of the curved outer end wall 27. Stated differently, the vertical side walls 19 of the tip portion 18 (FIG. 2) are eliminated such that the device 10' is substantially conical in shape, as shown in FIG. 7.

When the device 10' is in use, as shown in FIG. 8, the size of the vacuum cavity 42' is increased and the size of the vacuum cavity 21' is decreased, as compared to regions 42 and 21 in the embodiment of FIGS. 1–6, respectively. The above discussion of dimensions A, B and D in the device 10 pertains equally to dimensions A', B' and D' of the device 10'.

Having described the preferred embodiments of the invention, it will now become apparent to one of skill in the art that other embodiments incorporating their concepts may be used. It is felt therefore that these embodiments should not be limited to disclosed embodiments but rather should be limited only by the spirit and scope of the appended claims.

We claim:

1. A device for alleviating female urinary incontinence comprising:

a resilient and at least partially deformable device body having an enclosed distal tip portion, a flange and an intermediate frustoconical portion extending outwardly from said tip portion to said flange, wherein said flange extends substantially horizontal from said frustoconical portion and wherein said flange has an inner diameter and said intermediate frustoconical portion has walls having a length equal to or greater than one half of said inner diameter of said flange, wherein, in use, said device body is deformed such that wall portions of said intermediate frustoconical portion adjacent to said tip portion are moved toward abutting relation to form a first region within said tip portion and a second region within said intermediate frustoconical portion, and wherein the meatus of the user is disposed in said second region and is prevented from entering said first region by said wall portions of said intermediate frustoconical portion and wherein said device body is removed from the meatus of the user in order to permit voiding.

2. The device recited in claim 1 wherein said deformation of said device body causes a vacuum environment to be formed in said first and second regions by which a body contacting surface of said flange and a body contacting surface of said intermediate frustoconical portion are maintained in contact with the meatus of the user.

3. The device recited in claim 1 wherein said first and second regions are separated by a closure formed by abutment of said wall portions of said intermediate frustoconical portion.

4. The device recited in claim 1 wherein said device body further comprises a gripping portion to facilitate application and removal of said device.

5. A device for alleviating female urinary incontinence comprising:

a resilient and at least partially deformable device body having an enclosed distal tip portion, a flange and an intermediate frustoconical portion extending outwardly from said tip portion to said flange, wherein said flange extends substantially horizontal from said frustoconical portion and wherein said flange has an inner diameter and said intermediate frustoconical portion has walls having a length equal to or greater than one half of said inner diameter of said flange, wherein, in use, said frustoconical portion is deformed to form a broad based tent region having an apex at an end region of said intermediate frustoconical portion adjacent to said tip portion, said tent region being disposed over the meatus of the user, and wherein the meatus of the user is prevented from extending beyond said apex of said tent region into said tip portion and wherein said device body is removed from the meatus of the user in order to permit voiding.

6. The device recited in claim 5 wherein said deformation of said device body causes a vacuum environment to be formed in said tent region and said tip portion by which a body contacting surface of said flange and a body contacting surface of said intermediate frustoconical portion are maintained in contact with the meatus of the user.

7. The device recited in claim 5 wherein said tent region and said tip portion are separated by a closure formed by said apex.

8. The device recited in claim 5 wherein said device body further comprises a gripping portion to facilitate application and removal of said device.

9. The device recited in claim 5 wherein said intermediate frustoconical portion has side walls having a length selected to prevent said frustoconical portion from becoming coplanar with said flange.

10. A method for alleviating urinary incontinence of a female user comprising the steps of:

deforming a device body having a distal tip portion, a flange and an intermediate frustoconical portion extending outwardly from said tip portion to said flange, by moving wall portions of said intermediate frustoconical portion adjacent to said tip portion toward abutting relation to form a first region within said tip portion and a second region within said intermediate frustoconical portion in which the meatus of the user is disposed, wherein the meatus of the user is prevented from entering said first region by said wall portions of said intermediate frustoconical portion; and removing said device body from the meatus of the user to permit voiding.

11. The method of claim 10 wherein said deforming step causes a vacuum environment to be formed in said first and second regions by which a body contacting surface of said flange and a body contacting surface of said intermediate frustoconical portion are maintained in contact with the meatus of the user.

12. The method recited in claim 10 wherein said deforming step includes the step of separating said first and second regions by a closure formed by abutment of said wall portions of said intermediate frustoconical portion.

13. The method recited in claim 10 wherein said flange has an inner diameter and said method further comprises the step of forming said device body such that said intermediate frustoconical portion has side walls having a length equal to or greater than one-half of said inner diameter of said flange.

* * * * *